United States Patent
Chan et al.

(10) Patent No.: US 10,350,396 B2
(45) Date of Patent: Jul. 16, 2019

(54) VENT CAP FOR A EUSTACHIAN TUBE DILATION SYSTEM

(71) Applicant: Acclarent, Inc., Menlo Park, CA (US)

(72) Inventors: Randy S. Chan, San Jose, CA (US); Ketan P. Muni, San Jose, CA (US); Robert W. Flagler, Pleasanton, CA (US); Ali Eslambolchi, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 1025 days.

(21) Appl. No.: 14/317,269

(22) Filed: Jun. 27, 2014

(65) Prior Publication Data

US 2015/0374963 A1    Dec. 31, 2015

(51) Int. Cl.

| | | |
|---|---|---|
| *A61F 11/00* | (2006.01) | |
| *A61B 17/24* | (2006.01) | |
| *A61M 29/02* | (2006.01) | |
| *A61M 25/10* | (2013.01) | |
| *A61B 17/00* | (2006.01) | |

(52) U.S. Cl.
CPC ............ *A61M 29/02* (2013.01); *A61B 17/24* (2013.01); *A61F 11/004* (2013.01); *A61M 25/10* (2013.01); *A61B 2017/00907* (2013.01); *A61F 11/002* (2013.01)

(58) Field of Classification Search
CPC ......... A61B 17/24; A61B 2017/00907; A61M 29/02; A61M 25/10; A61F 11/002; A61F 11/004
See application file for complete search history.

(56) References Cited

U.S. PATENT DOCUMENTS 3,467,101 A * 9/1969 Raible ............... A61B 17/3207
                                                          604/915
4,779,625 A * 10/1988 Cole .................... A61B 5/0215
                                                          188/268

(Continued)

FOREIGN PATENT DOCUMENTS

| EP | 1060758 A1 | 12/2000 |
|---|---|---|
| WO | WO 03/020356 A1 | 3/2003 |

(Continued)

OTHER PUBLICATIONS

International Search Report dated Jul. 9, 2015, International Application No. PCT/US2015/033139, International filing date May 29, 2015.

(Continued)

*Primary Examiner* — Jing Rui Ou
(74) *Attorney, Agent, or Firm* — Frost Brown Todd LLC

(57) ABSTRACT

A device and method for dilating a Eustachian tube of a patient is disclosed. The device includes a guide catheter and a balloon dilation catheter. The balloon dilation catheter has an actuator that prevents injury to the middle ear. The balloon dilation catheter is slidably coupled with the guide catheter through the guide catheter lumen and is fully inserted into the guide catheter lumen when the distal side of the actuator is adjacent to the proximal end of the guide catheter. The method involves advancing the guide catheter and balloon dilation catheter through a nasal passage of the patient to dilate a portion of the Eustachian tube.

10 Claims, 12 Drawing Sheets

(56) References Cited

U.S. PATENT DOCUMENTS

| | | | | |
|---|---|---|---|---|
| 4,793,351 | A * | 12/1988 | Landman | A61M 25/10 604/915 |
| 5,066,284 | A * | 11/1991 | Mersch | A61M 25/0693 604/168.01 |
| 5,176,698 | A * | 1/1993 | Burns | A61M 25/104 604/913 |
| 5,676,346 | A * | 10/1997 | Leinsing | A61M 39/26 251/149.1 |
| 5,749,857 | A * | 5/1998 | Cuppy | A61M 25/0606 604/161 |
| 5,755,709 | A | 5/1998 | Cuppy | |
| 6,482,171 | B1 | 11/2002 | Corvi et al. | |
| 6,540,735 | B1 * | 4/2003 | Ashby | A61B 17/0057 604/15 |
| 2002/0193752 | A1 * | 12/2002 | Lynn | A61M 39/02 604/249 |
| 2003/0009128 | A1 * | 1/2003 | Ackerman | A61M 25/10 604/96.01 |
| 2003/0083621 | A1 * | 5/2003 | Shaw | A61M 25/0606 604/164.07 |
| 2005/0124932 | A1 * | 6/2005 | Foster | A61M 25/10 604/99.04 |
| 2005/0124935 | A1 * | 6/2005 | McMichael | A61M 25/0097 604/129 |
| 2006/0167438 | A1 * | 7/2006 | Kalser | A61B 5/205 604/544 |
| 2008/0172007 | A1 | 7/2008 | Bousquet | |
| 2008/0287906 | A1 * | 11/2008 | Burkholz | A61M 25/0097 604/500 |
| 2010/0274188 | A1 | 10/2010 | Chang et al. | |
| 2013/0030458 | A1 | 1/2013 | Drontle et al. | |
| 2013/0090609 | A1 * | 4/2013 | Sonderegger | A61M 39/22 604/256 |
| 2013/0274715 | A1 | 10/2013 | Chan et al. | |

FOREIGN PATENT DOCUMENTS

| | | |
|---|---|---|
| WO | WO 2004/030719 A2 | 4/2004 |
| WO | WO 2012/054140 A1 | 4/2012 |
| WO | WO 2013/155450 A1 | 10/2013 |

OTHER PUBLICATIONS

Japanese Notification of Reasons for Refusal dated Mar. 29, 2019 for Application No. 2017-521052, 4 pages.

* cited by examiner

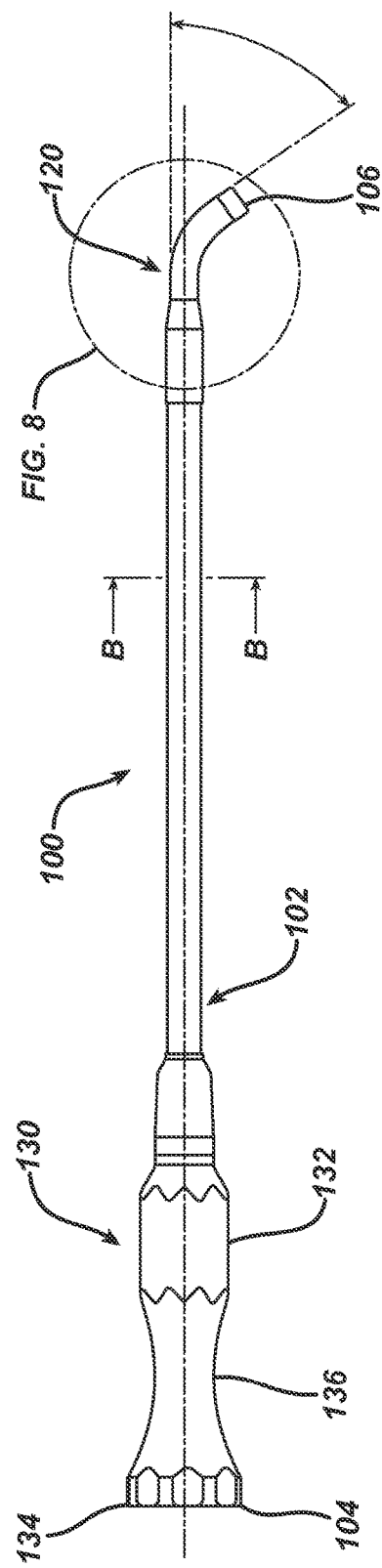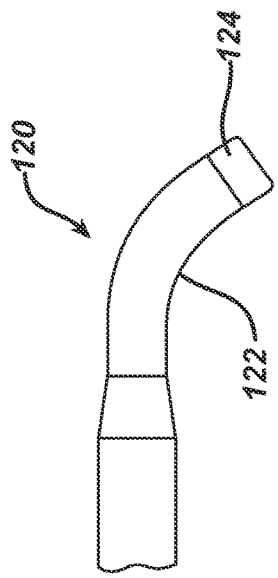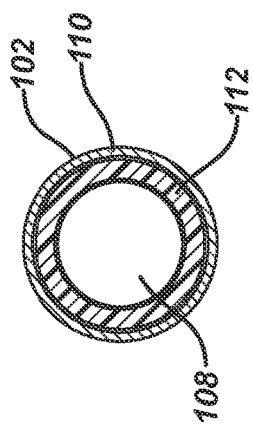

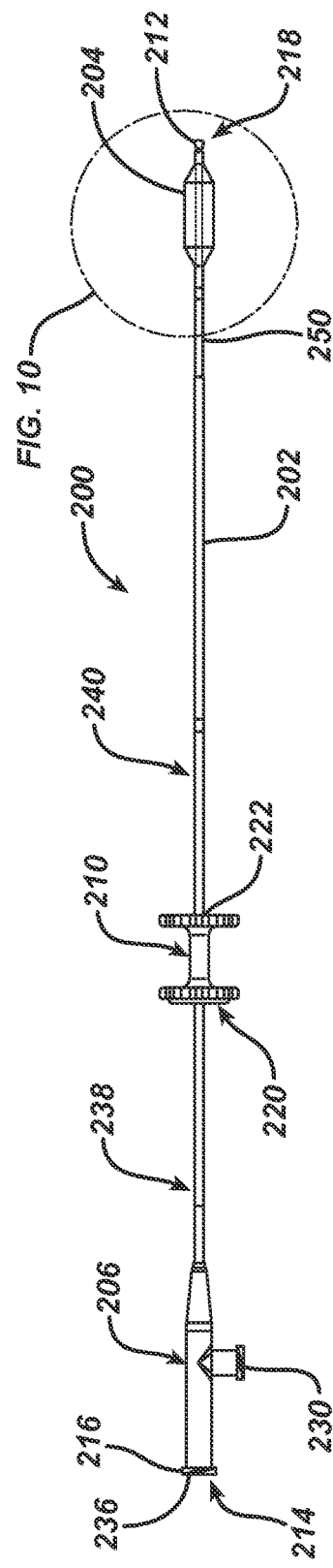
FIG. 9A
FIG. 9B
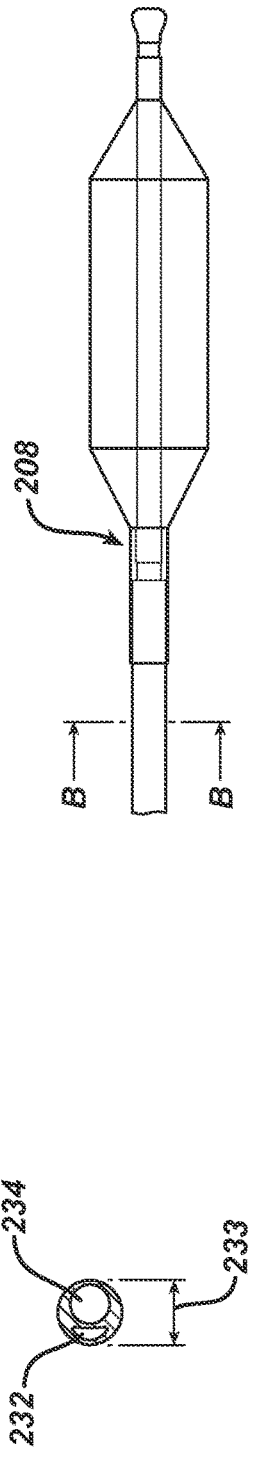
FIG. 10

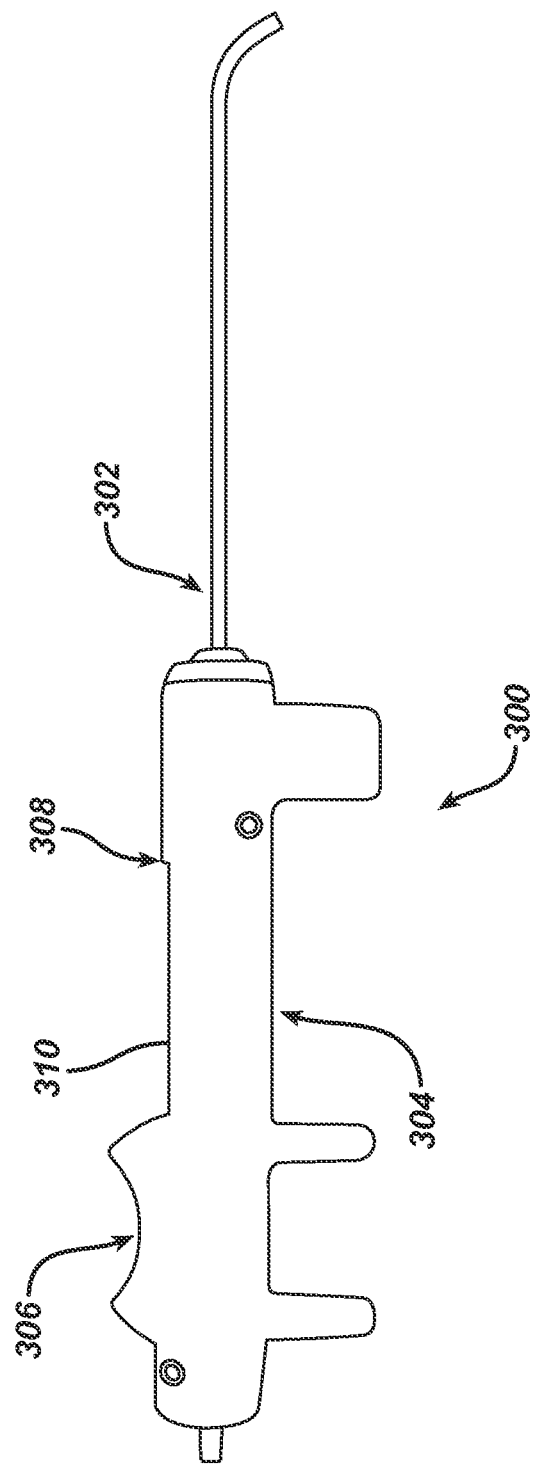

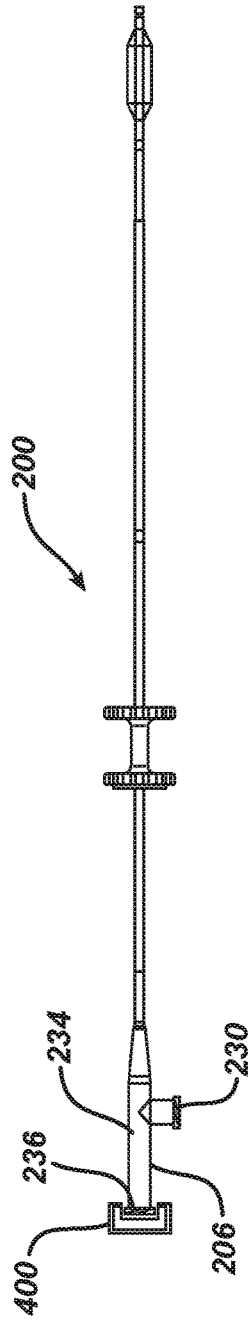
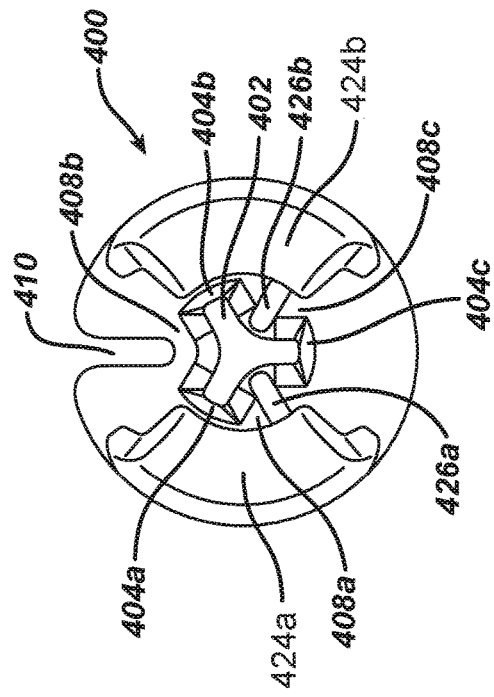
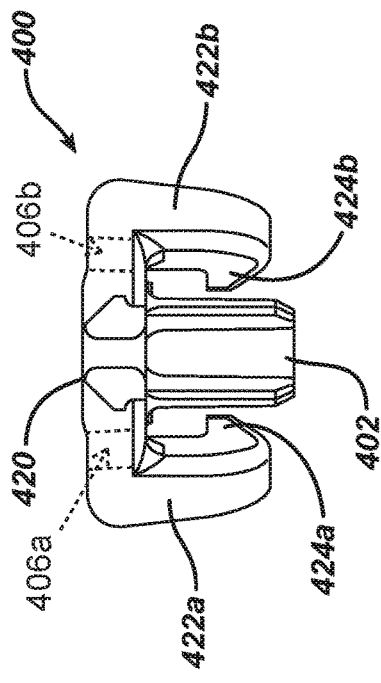

VENT CAP FOR A EUSTACHIAN TUBE DILATION SYSTEM

FIELD OF THE INVENTION

The present invention is related to methods and systems for accessing and treating target tissue regions within the middle ear and the Eustachian tube.

BACKGROUND OF THE INVENTION

Referring to FIGS. 1-2, the ear 10 is divided into three parts: an external ear 12, a middle ear 14 and an inner ear 16. The external ear 12 consists of an auricle 18 and ear canal 20 that gather sound and direct it towards a tympanic membrane 22 (also referred to as the eardrum) located at an inner end 24 of the ear canal 20. The middle ear 14 lies between the external and inner ears 12 and 16 and is connected to the back of the throat by a Eustachian tube 26 which serves as a pressure equalizing valve between the ear 10 and the sinuses. The Eustachian tube 26 terminates in a distal opening or ostium 28 in the nasopharynx region 30 of the throat 32. In addition to the eardrum 22, the middle ear 14 also consists of three small ear bones (ossicles): the malleus 34 (hammer), incus 36 (anvil) and stapes 38 (stirrup). These bones 34-38 transmit sound vibrations to the inner ear 16 and thereby act as a transformer, converting sound vibrations in the canal 20 of the external ear 12 into fluid waves in the inner ear 16. These fluid waves stimulate several nerve endings 40 that, in turn, transmit sound energy to the brain where it is interpreted.

The Eustachian tube 26 is a narrow, two to two-and-a-half centimeter long channel, measured from the ostium 28 to the bony isthmus 29, connecting the middle ear 14 with the nasopharynx 30, the upper throat area just above the palate, in back of the nose. The Eustachian tube 26 functions as a pressure equalizing valve for the middle ear 14 which is normally filled with air. When functioning properly, the Eustachian tube 26 opens for a fraction of a second periodically (about once every three minutes) in response to swallowing or yawning. In so doing, it allows air into the middle ear 14 to replace air that has been absorbed by the middle ear lining (mucous membrane) or to equalize pressure changes occurring on altitude changes. Anything that interferes with this periodic opening and closing of the Eustachian tube 26 may result in hearing impairment or other ear symptoms.

Obstruction or blockage of the Eustachian tube 26 results in a negative middle ear pressure 14, with retraction (sucking in) of the eardrum 22. In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear 14, creating a condition referred to as serous otitis media (fluid in the middle ear). This occurs frequently in children in connection with an upper respiratory infection and accounts for the hearing impairment associated with this condition.

A lining membrane (mucous membrane) of the middle ear 14 and Eustachian tube 26 is connected with, and is the same as, the membrane of the nose 42, sinuses 44 and throat 32. Infection of these areas results in mucous membrane swelling which in turn may result in obstruction of the Eustachian tube 26. This is referred to as serous otitis media, i.e. essentially a collection of fluid in the middle ear 14 that can be acute or chronic, usually the result of blockage of the distal opening 28 of the Eustachian tube 26 which allows fluid to accumulate in the middle ear 14. In the presence of bacteria, this fluid may become infected, leading to an acute suppurative otitis media (infected or abscessed middle ear). When infection does not develop, the fluid remains until the Eustachian tube 26 again begins to function normally, at which time the fluid is absorbed or drains down the tube into the throat 32 through the Eustachian tube opening 28.

Chronic serous otitis media may result from longstanding Eustachian tube blockage, or from thickening of the fluid so that it cannot be absorbed or drained down the Eustachian tube 26. This chronic condition is usually associated with hearing impairment. There may be recurrent ear pain, especially when the individual catches a cold. Fortunately, serous otitis media may persist for many years without producing any permanent damage to the middle ear mechanism. The presence of fluid in the middle ear 14, however, makes it very susceptible to recurrent acute infections. These recurrent infections may result in middle ear damage.

When the Eustachian tube 26 contains a build-up of fluid, a number of things will occur. First, the body absorbs the air from the middle ear 14, causing a vacuum to form which tends to pull the lining membrane and ear drum 22 inward, causing pain. Next, the body replaces the vacuum with more fluid which tends to relieve the pain, but the patient can experience a fullness sensation in the ear 10. Treatment of this condition with antihistamines and decongestants can take many weeks to be fully effective. Finally, the fluid can become infected, which is painful and makes the patient feel ill and which may cause the patient not to be able to hear well. If the inner ear 14 is affected, the patient may feel a spinning or turning sensation (vertigo). The infection is typically treated with antibiotics.

However, even if antihistamines, decongestants and antibiotics are used to treat an infection or other cause of fluid build-up in the middle ear 14, these treatments will typically not immediately resolve the pain and discomfort caused by the buildup of fluid in the middle ear 14; i.e. the most immediate relief will be felt by the patient if the fluid can be removed from the Eustachian tube 26.

Antibiotic treatment of middle ear infections typically results in normal middle ear function within three to four weeks. During the healing period, the patient can experience varying degrees of ear pressure, popping, clicking and fluctuation of hearing, occasionally with shooting pain in the ear. Resolution of the infection occasionally leaves the patient with uninfected fluid in the middle ear 14, localized in the Eustachian tube 26.

Fluid build-up caused by these types of infections has been treated surgically in the past. The primary objective of surgical treatment of chronic serous otitis media is to reestablish ventilation of the middle ear, keeping the hearing at a normal level and preventing recurrent infection that might damage the eardrum membrane and middle ear bones.

For example, as shown in FIG. 3, a myringotomy can be performed to relieve fluid in the middle ear 14. A myringotomy is an incision 42 in the eardrum 22 performed to remove fluid in the middle ear 14. A hollow plastic tube 44, referred to as a ventilation tube, is inserted and lodged in the incision 42 to prevent the incision 42 from healing and to ensure ventilation of the middle ear 14. The ventilation tube 44 temporarily takes the place of the Eustachian tube 26 in equalizing the pressure in the middle ear 14. The ventilation tube 44 usually remains in place for three to nine months during which time the Eustachian tube 26 blockage subsides. When the tube 44 dislodges, the eardrum 22 heals; the Eustachian tube 26 then resumes its normal pressure equalizing function.

Another method of relieving the pressure in the middle ear 14 is shown in FIG. 4 in which a hypodermic needle 46 is driven through the eardrum 22 through which any accumulated fluid can be withdrawn from typically only the upper portion of the Eustachian tube 26.

The methods of FIGS. 3 and 4 involve rupturing the eardrum 22 to relieve the fluid accumulation and pressure increase in the middle ear. Neither of these methods, in addition to the sometimes permanent puncture created in the eardrum 22, is especially effective in removing all of the fluid in the Eustachian tube 26 since often the lower end 28 thereof is blocked and dammed with fluid.

In connection with the above surgical treatments of FIGS. 3 and 4, Eustachian tube 26 inflation is also employed to relieve the pressure build-up and fluid accumulation as shown in FIG. 5. The hypodermic syringe 46 (shown with a flexible tip 48) is inserted into a nostril or into the mouth until the tip 48 is positioned adjacent the distal opening 28 of the Eustachian tube 26 in the nasopharynx region 30 of the throat 32. Air is blown through the tip 48 via the syringe 46 into the obstructed Eustachian tube 26 and, thus, into the middle ear 14 to help relieve the congestion and reestablish middle ear ventilation. This procedure is often referred to as politzerization. Politzerization is most effective when one of the nostrils is pinched shut (as shown in FIG. 6), while the patient simultaneously swallows. This procedure forces air into the Eustachian tube 26 and the middle ear 14. This technique is good for opening the Eustachian tube 26 but it does not clear accumulated fluid away.

Another method for clearing the middle ear 14 (at least temporarily) is referred to as the "valsalva" maneuver, accomplished by forcibly blowing air into the middle ear 14 while holding the nose, often called popping the ear. This method is also good for opening the Eustachian tube 26 but it does not clear the accumulated fluid away either.

Typical disorders associated with the middle ear and the Eustachian tube include perforated ear drums, tympanosclerosis, incus erosion, otitis media, cholesteotoma, mastoiditis, patulous Eustachian tube, and conductive hearing loss. To treat some of these disorders, ear surgery may be performed. Most ear surgery is microsurgery, performed with an operating microscope. Types of ear surgery include stapedectomy, tympanoplasty, myringotomy and ear tube surgery.

One of the simplest ear surgeries is the myringotomy or the incision of the ear drum. However, ear surgery can also require the removal of the tympanic membrane for the visualization of the middle ear space. Often surgeons will try to preserve the integrity of the membrane by making incisions in the skin of the ear canal and removing the tympanic membrane as a complete unit. Alternatively, middle ear access is achieved via the mastoids. This method approaches the middle ear space from behind the ear and drills through the mastoid air cells to the middle ear. Whether the bony partition between the external ear canal and the mastoid is removed or not depends on the extent of the disease. Canal-wall-down refers to the removal of this bony partition. Canal-wall-up refers to keeping this bony partition intact. The term modified radical mastoidectomy refers to an operation where this bony partition is removed and the eardrum and ossicles are reconstructed. A radical mastoidectomy is an operation where this bony partition is removed and the ear drum, malleus and incus bones are permanently removed so that the inner lining of the large cholesteotoma sac can be safely cleaned. This operation is done when an extensive cholesteotoma is encountered or one that is adherent to the inner ear or facial nerve.

Afflictions of the middle ear and Eustachian tube are very prevalent and a serious medical problem, afflicting millions of people and causing pain, discomfort and even hearing loss or permanent ear damage. Although a number of treatments have been developed, as described above each of them have shortcomings. Therefore, a need exists for improved methods and systems for accessing, diagnosing and treating target tissue regions within the middle ear and the Eustachian tube. Ideally, such methods and systems would be minimally invasive and pose very little risk of damage to healthy ear tissue.

US Patent Publication No. 2010/0274188, now abandoned, which is incorporated by reference herein in its entirety is directed toward methods and systems for accessing, diagnosing and treating target tissue regions within the middle ear and the Eustachian tube. One particular method described in the publication is for dilating a Eustachian tube of a patient. A guide catheter may be advanced through a nasal passage of the patient to position a distal end of the guide catheter at or near an opening of the Eustachian tube of the patient. A distal portion of the guide catheter may include a bend having an angle between 30 and 90 degrees. The distal portion may be more flexible than a proximal portion of the guide catheter. A guidewire may be advanced through the guide catheter such that a distal end of the guidewire enters the Eustachian tube. A dilation catheter may be advanced over the guidewire to position a dilator of the dilation catheter within the Eustachian tube. The dilator may be expanded to dilate the Eustachian tube. The dilation catheter and guidewire may be removed from the patient.

Improvement in the devices described above would provide a system for dilation of the Eustachian tube that would be ergonomic and easy to use and would safely and effectively access the Eustachian tube without the need for a guidewire.

SUMMARY OF THE INVENTION

The present invention provides systems and devices for accessing and treating the Eustachian tube of a patient.

In one aspect, a system for use in dilating a Eustachian tube of a patient includes a balloon dilation catheter for accessing and treating the Eustachian tube through the nose of a human patient. The balloon dilation catheter comprises an elongate shaft having a proximal end and a distal end and inflation lumen therebetween, an inflatable balloon positioned at the distal end of said elongate shaft, a proximal connecter positioned at the proximal end of said elongate shaft, said proximal connector comprising an inflation port in fluid communication with the inflation lumen of the elongate shaft and an in-line port; and a vent cap attached to said in-line port.

In one embodiment, the attachment of the vent cap to the in-line port is reversible. In another embodiment, the vent cap is fixedly attached to the in-line port. In a further embodiment, the vent cap comprises one or more vent portions. In yet another embodiment 1 wherein the vent cap comprises a top portion, a central post and a side portion, wherein the central post is dimensioned for insertion into the in-line port. The side portion may include at least two side arms with gripping features for gripping to the in-line port.

In a second aspect, the invention includes a vent cap for attachment to an in-line port of a balloon catheter, the in-line port having an lumen and an outside surface, the balloon catheter further having in inflation port. The vent cap includes a top portion, a central post dimensioned for insertion into the lumen of the in-line port of the balloon catheter; and a side portion dimensioned to grip the outside surface of the in-line port.

In one embodiment, the attachment of the vent cap to the in-line port is reversible. In another embodiment, the vent cap is fixedly attached to the in-line port. In a further embodiment, the vent cap comprises one or more vent portions. In yet another embodiment 1 wherein the vent cap comprises a top portion, a central post and a side portion, wherein the central post is dimensioned for insertion into the in-line port. The side portion may include at least two side arms with gripping features for gripping to the in-line port.

For a further understanding of the nature and advantages of the invention, reference should be made to the following description taken in conjunction with the accompanying figures. Each of the figures is provided for the purpose of illustration and description only and is not intended to limit the scope of the embodiments of the present invention.

BRIEF DESCRIPTION OF THE DRAWINGS

FIG. 7A is a simplified side view of a guide catheter useful for positioning the catheter of FIG. 9A.

FIG. 7B is a cross-sectional view of the guide catheter shown in FIG. 7A through line B-B of FIG. 7A.

FIG. 8 is an enlarged view of the distal end of the guide catheter shown in FIG. 7A.

FIG. 9A is a simplified side view of a balloon dilation catheter according to an embodiment of the present invention.

FIG. 9B is a cross-sectional view of the balloon dilation catheter shown in FIGS. 9A and 10 through line B-B of FIG. 10.

FIG. 10 is an enlarged view of the distal end of the balloon dilation catheter shown in FIG. 9A.

FIG. 11 is a simplified view of a guide catheter according to a further embodiment of the invention.

FIG. 12 is a further view of the balloon dilation catheter of FIG. 9A including the vent cap of the current invention.

FIG. 13A is a side view and FIG. 13B is a bottom view of the vent cap shown in FIG. 12.

DETAILED DESCRIPTION OF THE INVENTION

Figure 1:
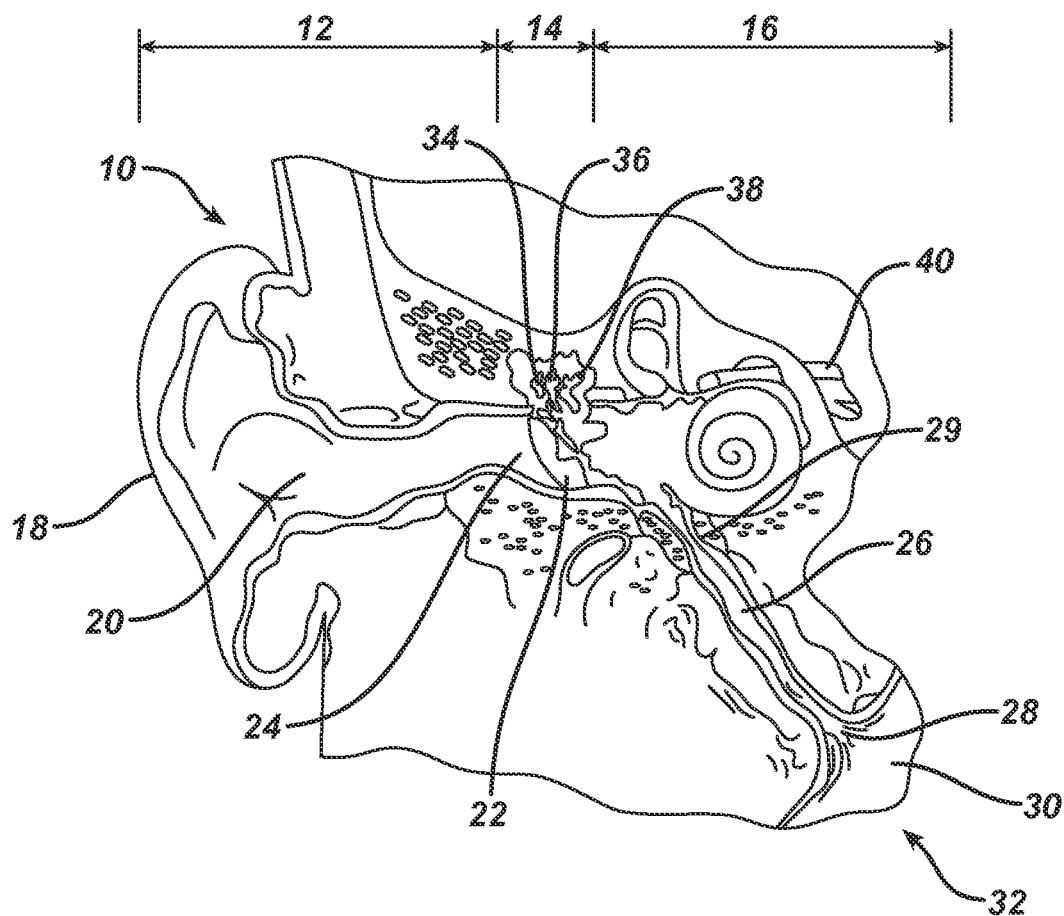
FIG. 1 is a cross-section of a human ear showing the inner, middle and outer ear portions and the Eustachian tube connecting the middle ear with the nasopharynx region of the throat via a distal opening thereof.
Figure 2:
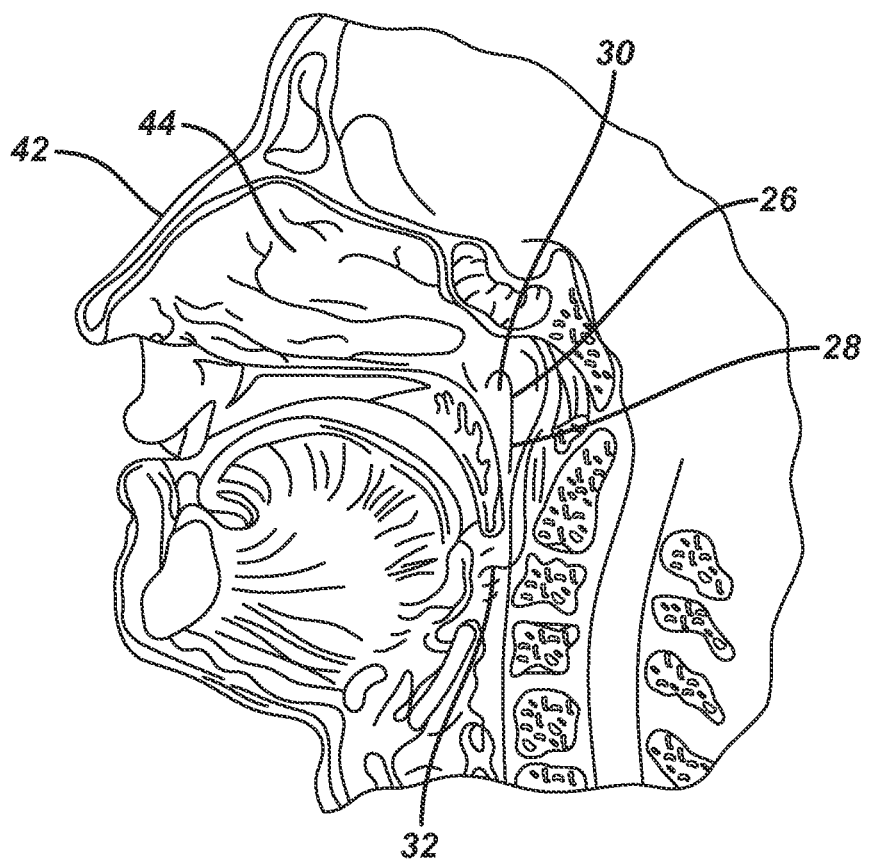
FIG. 2 is a cross-section of a human head showing the nasopharynx region of the throat illustrated in FIG. 1 containing the distal opening of the Eustachian tube illustrated in FIG. 1.
Figure 3:
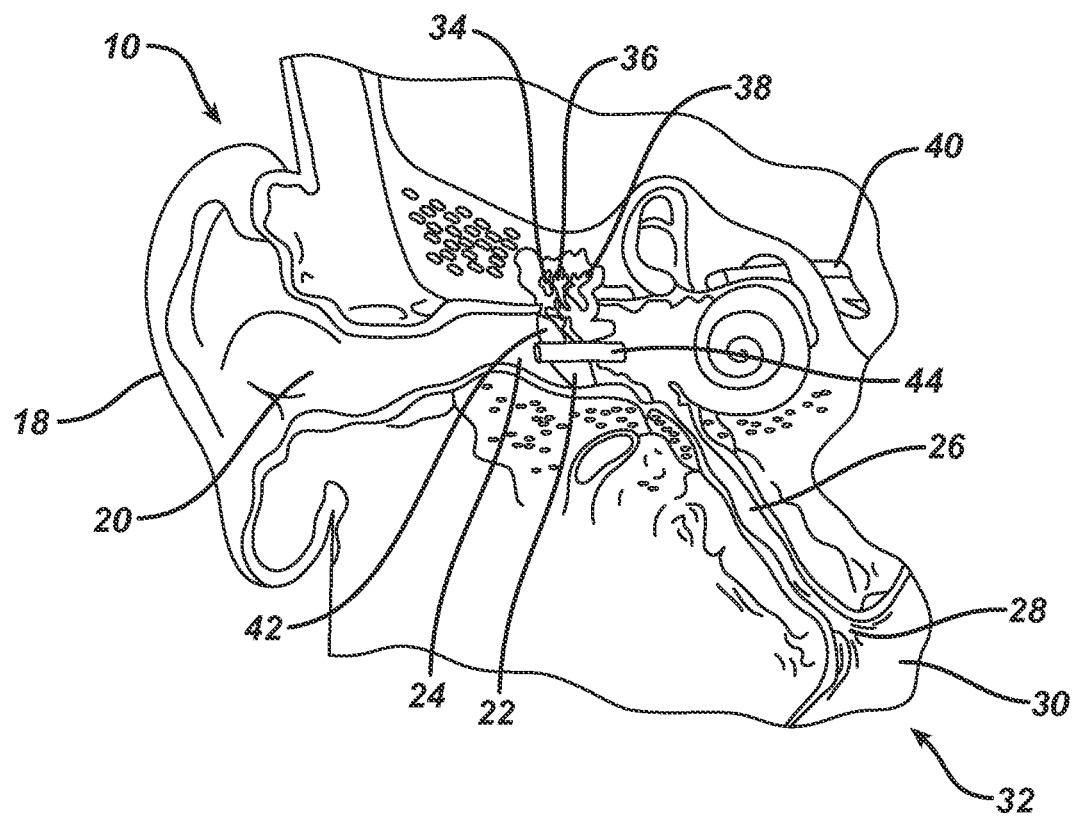
FIG. 3 is a cross-section of a human ear in the orientation shown in FIG. 1 showing a prior art surgical method for relieving fluid in the middle ear in which a ventilation tube is placed within an incision in the eardrum.
Figure 4:
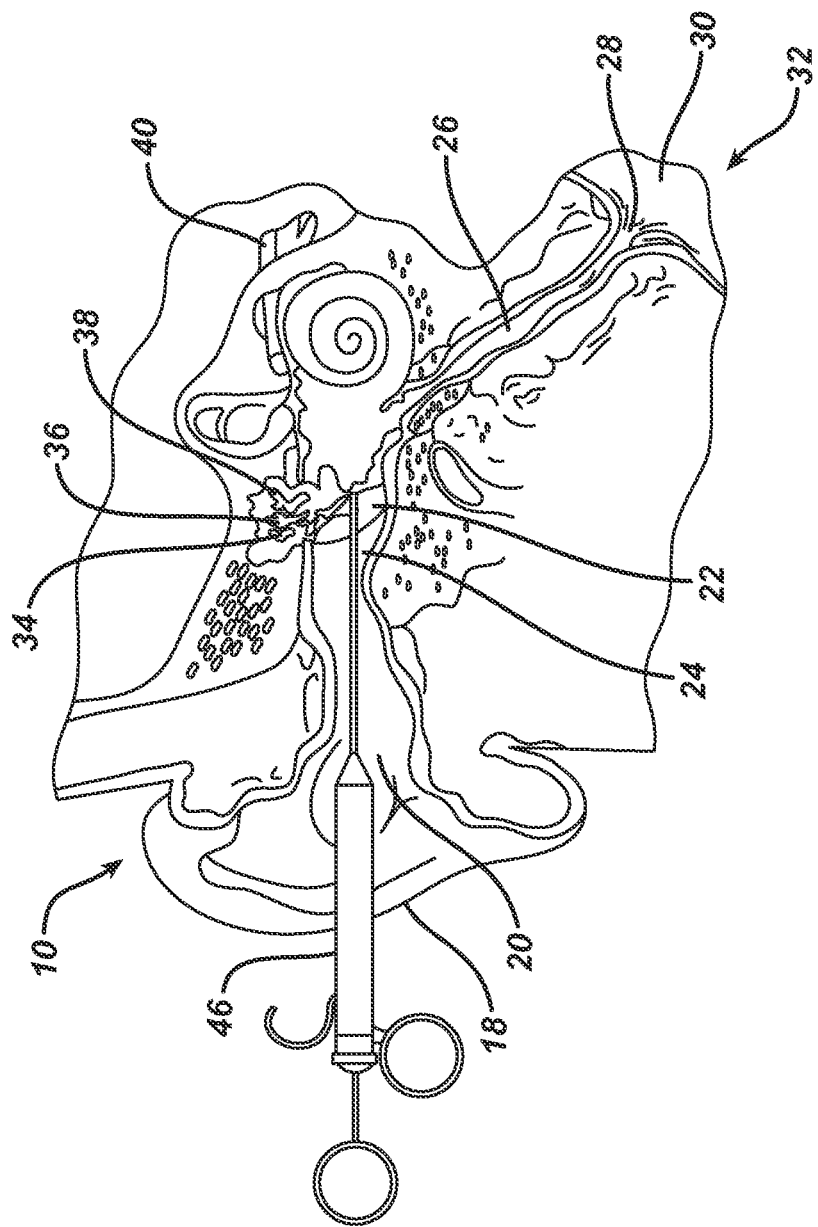
FIG. 4 is a cross-section of a human ear in the orientation shown in FIG. 1 showing a prior art surgical method for relieving fluid in the middle ear in which a syringe is shown having a needle perforating the eardrum.
Figure 5:
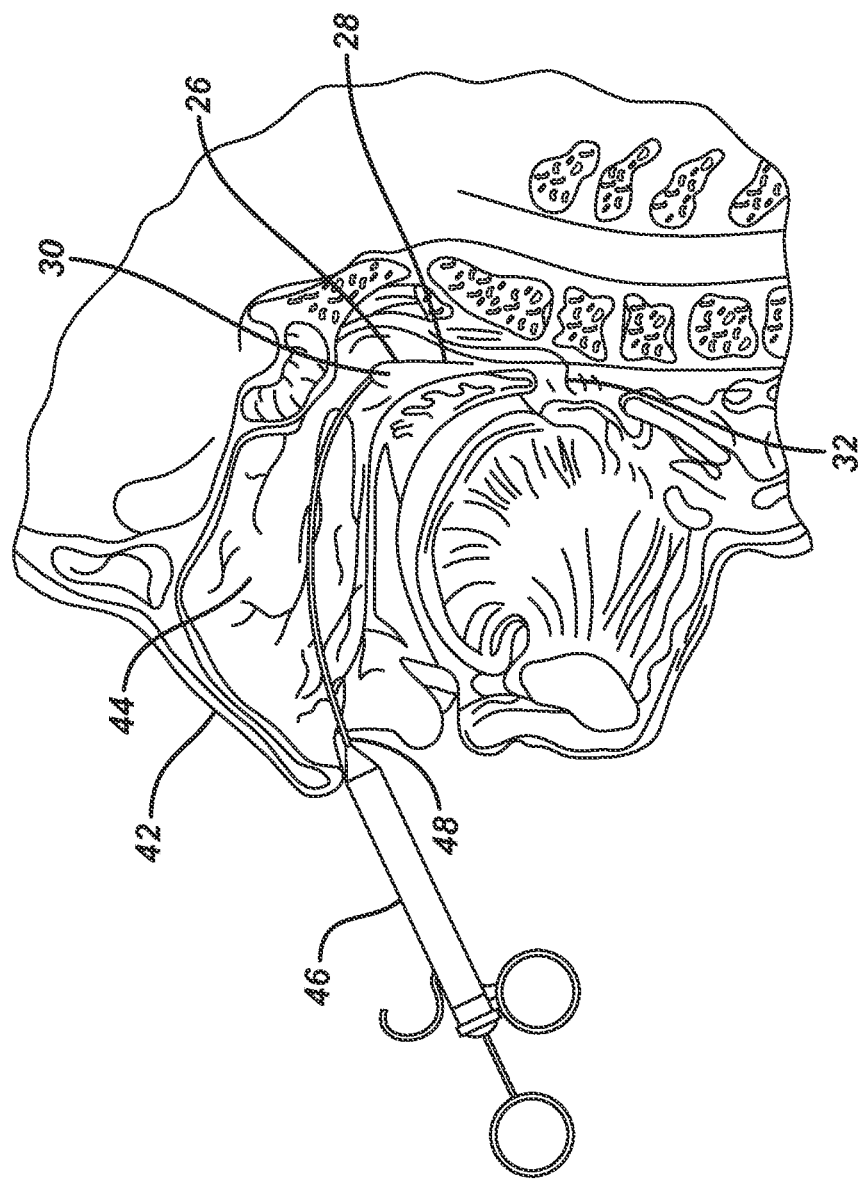
FIGS. 5-6 show a cross-section of a human head in the orientation shown in FIG. 2 showing a prior art politzeration method for relieving fluid in the middle ear in which a syringe is shown having a flexible tip extending into the nose and/or throat area so that the tip abuts the distal opening of the Eustachian tube while the nose is plugged.
Figure 6:
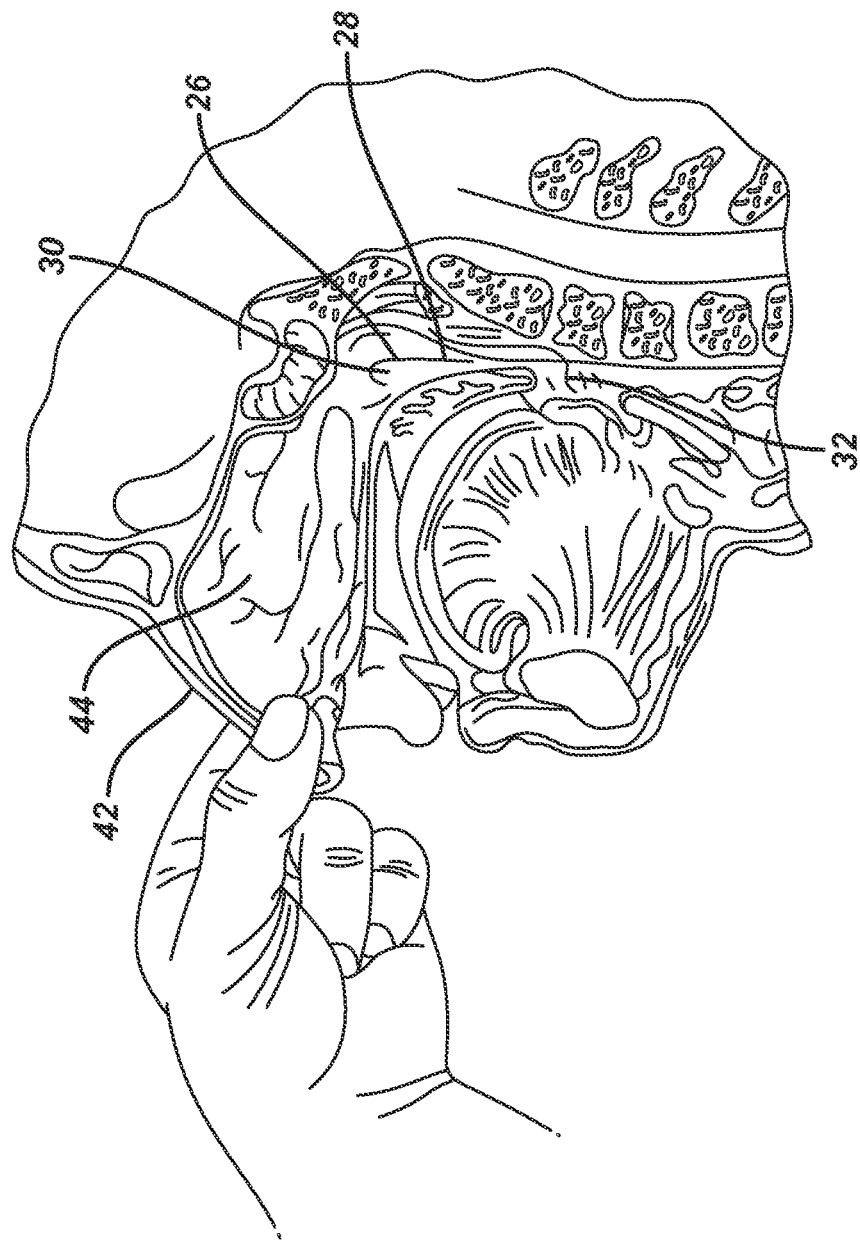

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternative and uses of the invention, including what is presently believed to be the best mode of carrying out the invention.

As used herein, the terms "about" and "approximately" for any numerical values or ranges indicate a suitable dimensional tolerance that allows the part or collection of components to function for its intended purpose as described herein.

The embodiments of the present invention are directed toward methods and systems for easily accessing and treating target tissue regions within the middle ear and the Eustachian tube using a system that can be operated with one hand and without damaging structures in the middle ear.

In various alternative embodiments the invention includes a guide catheter 100 and a balloon dilation catheter 200 operable in combination with a single hand.

One embodiment of the guide catheter 100 of the invention is shown in FIG. 7A. As shown, the guide catheter 100 includes an elongate tubular shaft 102 that has a proximal end 104, a distal end 106 and a lumen 108 therebetween. The guide catheter 100 may have any suitable length, diameter, angle of bend, and location of the bend along the length of the catheter 100, to facilitate accessing a Eustachian tube opening. In some embodiments, for example, the guide catheter 100 may have a length between about 8 cm and about 20 cm, and more preferably between about 10 cm and about 15 cm and often about 11 cm.

FIG. 7B is a cross-sectional view of the guide catheter elongate tubular shaft 102. As can be seen, the shaft has an outer shaft tube 110, an inner shaft tube 112 and a lumen 108. The outer shaft tube 110 may be constructed of a stiff material such as stainless steel and the inner shaft tube 112 may be constructed of a more flexible material such as a polymeric material including but not limited to nylon and further including a PTFE liner. The lumen 108 has a diameter of between about 2 mm and 3 mm preferably between about 2.5 mm and 2.6 mm such that the balloon dilation catheter 200 can be easily inserted into the lumen 108 for dilation of the Eustachian tube 26. The combination guide catheter 100 and balloon catheter 200 may a compact system that is designed for a one-handed procedure. By compact is intended that the length of the guide catheter shaft that is distal of the bend in the guide catheter is between about 0.5 and 2.0 cm, often between about 1 and 2 cm and often about 1 cm. The compactness helps reduce interference with other instruments, such as an endoscope that may be used to help in visualizing the positioning of the system.

The distal portion 120 of guide catheter 100 is shown in an enlarged view in FIG. 8. The distal portion 120 of the guide catheter 100 may have a bend 122 with an angle between about 45 degrees and about 65 degrees, and more preferably between about 50 degrees and about 60 degrees and often about 55 degrees to facilitate access into the Eustachian tube 26. The distal portion 120 of the guide catheter 100 is made of a transparent material such as a polymer including but not limited to nylon and PTFE such that the balloon dilation catheter is visible within the distal portion 120 and is more flexible than the elongate shaft 102. The distal tip 124 of the distal portion 120 of the guide catheter 100 is made of pebax such that it provides for atraumatic access to the Eustachian tube, and may contain 20% barium sulfate or other similar radiopaque materials for visualizable access.

Referring again to FIG. 7A, the proximal portion 130 of guide catheter 100 includes a proximal hub 132 to aid in insertion of the balloon catheter into the Eustachian Tube 26. The hub 132 has a larger diameter proximal end 134 and a smaller diameter middle section 136 to facilitate stabilization of the guide catheter 100 in the nose, rotation of the guide catheter 100 and insertion of the balloon catheter 200 as will be described in further detail below. The hub 132 is ergonomically designed for insertion, location and rotation with slight manipulations with one hand.

A further embodiment of the guide catheter 300 according to the invention is shown in FIG. 11. In this embodiment, the proximal hub is a handle. The guide catheter comprises an elongate shaft 302 and a handle 304 to aid in insertion of the balloon catheter (not shown) into the Eustachian Tube 26 in a manner similar to that described below with regard to the guide catheter shown in FIG. 7A. In the embodiment shown in FIG. 11, the actuator 302 comprises a slider that is attached to the balloon catheter that is contained within the handles 304 and is slidably contained within the elongate shaft 302 of the guide catheter. In use, the guide catheter is inserted into the sinus of the patient and the balloon catheter is advanced into the Eustachian tube via thumb or single finger advancement of the actuator 302 along the handle 304. The advancement of the balloon catheter is continued until a visual marker indicates that advancement is complete, or until the enlarged tip of the balloon catheter abuts the isthmus of the Eustachian tube or the actuator abuts the distal end 308 of the opening 310 in the handle 304 and is therefore fully deployed.

The balloon dilation catheter of the invention is shown in FIG. 9A. The balloon dilation catheter 200 generally includes an elongate shaft 202 having a proximal end 214 and a distal end 218. The balloon dilation catheter 200 further includes a balloon 204 on the distal end 218 of the elongate shaft 202. The balloon 204 may be a polymer balloon (compliant, semi-compliant or non-compliant). In one embodiment, the balloon may be a suitable non-compliant material such as but not limited to polyethylene terephthalate (PET). PEBAX, nylon or the like. The balloon catheter may include any size of balloon including but not limited to balloons of 2 mm to 8 mm in diameter or of between about 5 mm and 6 mm (when inflated) and 12 mm to 24 mm in working length (for example 2 mm×12 mm, 3.5 mm×12 mm, 5 mm×16 mm, 5 mm×24 mm, 6 mm×16 mm, 6 mm×20 mm, 6 mm×24 mm, 7 mm×16 mm and 7 mm×24 mm). The balloon dilation catheter 200 generally includes a proximally located connection 230 for inflating/activating the balloon 204.

The balloon 204 may be expanded to dilate the Eustachian tube ET after it is placed in a desirable location therein. For example, the opening area of the Eustachian tube ET includes a pharyngeal ostium, and the dilation catheter 200 may be advanced to position the balloon in the pharyngeal ostium. An endoscope may be used to assist in positioning the dilation catheter 200. The endoscope may be advanced through the nasal passage to view the dilation catheter 200. A marker 208 on a shaft of the dilation catheter 200 can be viewed from the endoscope to approximate a location of the balloon 204 relative to the opening of the Eustachian tube ET based on a distance of the marker 208 from a proximal end of the balloon 204. Accordingly, the dilation catheter 200 can be moved to place the marker in a desirable location before expansion of the balloon 204 in the Eustachian tube ET.

The balloon dilation catheter further includes an actuator 210. The actuator 210 has a proximal side 220 and a distal side 222. In the embodiment shown in FIG. 9A, the actuator 210 is secured by an adhesive to the elongate shaft 202. The portion 240 of the elongate shaft 202 that is distal of the actuator 210 is sufficiently stiff to be guided through the nasal cavity and into the Eustachian Tube and is constructed of stainless steel and preferably includes a stainless steel hypotube. The portion 238 of the elongate shaft 202 that is proximal of the actuator 210 and that portion 250 that is distal of portion 240 is more flexible than the portion 240 and is constructed of a polymeric material including but not limited to pebax. In this way, the proximal portion 238 of the elongate shaft 202 will not interfere with the endoscope described above as it is advanced through the nasal passage such that the dilation catheter 200 can be easily viewed. The actuator 210 allows for easy, ergonomic one-handed advancement of the dilation 200 catheter through the guide catheter 100 and into the Eustachian Tube ET. The actuator 210 may be used to advance or retract in alternative ways including but not limited to use of the thumb, the index finger, or a combination of fingers (i.e. the index and middle fingers) or the thumb and the index or middle finger.

The distal end 218 of the balloon catheter 200 further includes a tip 212 and a flexible shaft portion 250 that is constructed of a polymeric material including but not limited to pebax that extends from the distal end of the elongate shaft 202 to the proximal end of the balloon 204. In the embodiment shown in FIG. 9A, the tip 212 is a bulbous polymeric blueberry shaped tip that is atraumatic and is about 1.5 mm to 2 mm in length with an outer diameter of between about 2 mm and 3 mm. The smoothness and roundness of tip 212 facilitates advancement of the balloon catheter 200 by helping it glide smoothly through the Eustachian Tube ET. The tip further acts as a safety stop. The isthmus 29 of the Eustachian Tube, shown in FIG. 1 is approximately 1 mm in diameter. The tip diameter is larger than the outer diameter 233 of the elongate shaft 202 shown in cross-section in FIG. 9B such that the tip 212 size will prevent the balloon catheter 200 from passing through the isthmus 29 into the middle ear 14.

The balloon 204 may be held in location while in an expanded state for an extended period of time (e.g. several seconds or minutes). The balloon catheter 200 may also deliver a substance to the Eustachian tube ET, such as one or more of the therapeutic or diagnostic agents described herein. The balloon 204 may also carry an expandable stent for delivery into the Eustachian tube upon expansion of the balloon 204. The balloon dilation catheter 200 and the guide catheter may be removed from the patient after the balloon 204 has been deflated/unexpanded. The Eustachian tube will resume functioning, normally opening and closing to equalize atmospheric pressure in the middle ear and protect the middle ear from unwanted pressure fluctuations and loud sounds.

In use, the guide catheter 100 may be advanced into a nostril and through a nasal cavity to position a distal end of the catheter 100 at, in or near an opening into the Eustachian tube. In one embodiment, the guide catheter 100 may be passed through a nostril to the Eustachian tube on the ipsilateral (same side) of the head. In an alternative embodiment, the guide catheter 100 may be passed through a nostril to the Eustachian tube on the contralateral (opposite side) of the head. A guiding element such as a guidewire or illuminating fiber may be used to aid in accessing the Eustachian Tube.

After the guide catheter 100 is in a desired position, a balloon catheter 200 is advanced through the guide catheter 100 to position a balloon 204 of the balloon catheter 200 within the Eustachian tube ET. The physician/user may place the index and middle fingers on either side of the smaller diameter middle section 136 of the proximal hub 132 of the guide catheter 100. The physician/user will then place the thumb on the proximal side 220 of the actuator 210 or within both sides of the actuator 210 and will use the thumb to slide the balloon dilation catheter 200 through the guide catheter 100 to position the balloon within the Eustachian tube ET. Alternatively, the user may grasp the proximal hub 132 of the guide catheter 100 and use the index finger placed on the proximal side 220 of the actuator 210 or in between the distal side 222 and the proximal side 220 of the actuator 210 to advance the balloon catheter 200. The larger diameter tip 212 prevents the balloon catheter 200 from advancing too far into the middle ear. Further, the distal side 222 of the actuator 210 will bottom out against the proximal end 104 of the guide catheter 100, such that the balloon catheter cannot advance any further. The actuator 210 prevents the catheter from reaching too far into the middle ear, which can cause damage to structures in the middle ear. Further the actuator 210 can be positioned at the appropriate distance along the elongate shaft 202 such that access to the Eustachian tube may be from the contralateral or the ipsilateral side.

In an alternative embodiment, a balloon catheter 200 is advanced into a nostril of a patient without the use of a guide catheter. The balloon 204 of the balloon catheter 200 is placed within the Eustachian tube ET. The physician/user will advance the balloon catheter 200 until the proximal side 220 of the actuator 210 is adjacent the patient's nostril. The distal side 222 of the actuator 210 will bottom out against the patient's nostril, such that the balloon catheter cannot advance any further. The actuator 210 prevents the catheter from reaching too far into the middle ear, which can cause damage to structures in the middle ear. Further the actuator 210 can be positioned at the appropriate distance along the elongate shaft 202 such that access to the Eustachian tube may be from the contralateral or the ipsilateral side.

Following placement of the balloon catheter into the desired position any number of procedures may be carried out. The elongate shaft 202 contains adjacent dual lumen tubing (see FIG. 9B). By adjacent dual lumen tubing is intended that the lumens are next to each other but are spaced apart, one from the other. The inflation lumen 232 is used for inflation of the balloon with water, contrast medium or saline through inflation port 230 to a pressure of between about 3 and 15 atmospheres, or of between about 6 and 12 atmospheres. The injection lumen 234 permits the optional injection of water, medicament, or even the introduction of a guidewire through the in-line port 236 at the proximal end 216 of the proximal connector 206. In order to ensure that the inflation port 230 is the only port used for balloon inflation, the inflation port 230 and the in-line port 236 may optionally be different type connectors. For example, the inflation port may be a female connector whereas the in-line port is a male connector or vice versa. Alternatively, the in-line port may be a right-handed thread connector and the inflation port may have a left-handed thread connector or vice versa.

As an alternative or in addition to providing different types of connectors on the proximal connector 206, it may be desirable to include a vent cap 400 attached to the in-line port 236 as shown in FIG. 12. In the embodiment shown in FIG. 12, the vent cap 400 is snapped or bonded into place and is not removable or it is integrally formed with the proximal connector 206, so that there can be no inadvertent insertion of inflation medium, guidewire or other substance or device into the balloon catheter 200 and/or into the Eustachian tube. The vent cap 400 may be fixedly attached to the in-line port or it may be attached such that it is difficult to remove.

The vent cap 400 includes a central post 402 that is inserted into the in-line port 236 of the proximal connector 206 such that the vent cap 400 is axially aligned with the injection lumen 234 of the balloon catheter 200. In the embodiment shown in FIGS. 13A and 13B, the central post 402 is in a three clover arrangement. The three leaves, 404a, 404b, and 404c of the central post 402 are seated inside the injection lumen 234. The vent cap 400 further includes two elongate vent openings 406a and 406b such that a pathway exists between the open areas 408a, 408b and 408c between the leaves 404a, 404b and 404c and the elongate vent openings 406a and 406b located on the top portion 420 of the vent cap 400. A further vent opening 410 on the top portion 420 ensures a composite minimum vent area of at least four times that of the cross-sectional area of the injection lumen 234. The vent cap 400 may be of similar polymeric material as the proximal connector 400, and may be transparent for ease of visualization.

The vent cap 400 further includes two side arms 422a and 422b that form an integral unit with the top portion 420 and the central post 402. The side arms have gripping features 424a and 424b that grip or snap fit onto the in-line port 236 (for example latching under the threads of the in-line port 236). The vent cap 400 includes two stand-off features 426a and 426b that inhibit the vent cap 400 from seating directly against the in-line port 236, further ensuring the minimum vent area described above. In an alternative embodiment, the vent cap may contain a guidewire lumen for insertion of a guidewire. In this embodiment, a small lumen, of between 20 and 50 mm or of between 38 and 42 mm diameter extends through the top portion 420 and central post 402 of the vent cap. The guidewire may be inserted and removed through the guidewire lumen. The guidewire lumen may contain a feature such as an adjustable stop device, for example, a guidewire torquer with a collet that squeezes onto the guidewire and for maintaining the guidewire in position in the Eustachian tube and preventing it from moving further distally. Instead of a collet, the device may consist of a squeezable O-ring that compresses onto the guidewire when squeezed. In addition, the guidewire torquer may be locked onto the vent cap to keep the guidewire from moving proximally. Alternatively, an O-ring feature or collet may be incorporated in the vent cap. In this case, by twisting the vent cap, the O-ring or collet will squeeze onto the guidewire to keep it in place. In addition to or instead or inserting a guidewire into the guidewire lumen, a solution may be injected through the guidewire lumen as further described below.

As noted above, the vent cap 400 may be reversibly or irreversibly attached to the proximal connector. A vent cap that is reversibly attached to the balloon catheter proximal connector may be removed before or after balloon dilation of the Eustachian Tube. The vent cap would ensure the proper attachment of the inflation device or syringe to the inflation port 230 and not to the in-line port 236. Once the inflation device or syringe is attached to the inflation port, either prior to or following balloon dilation, the vent cap 400 could be removed and irrigation fluid or other solutions as described below could be delivered to the Eustachian tube.

Figure 14:
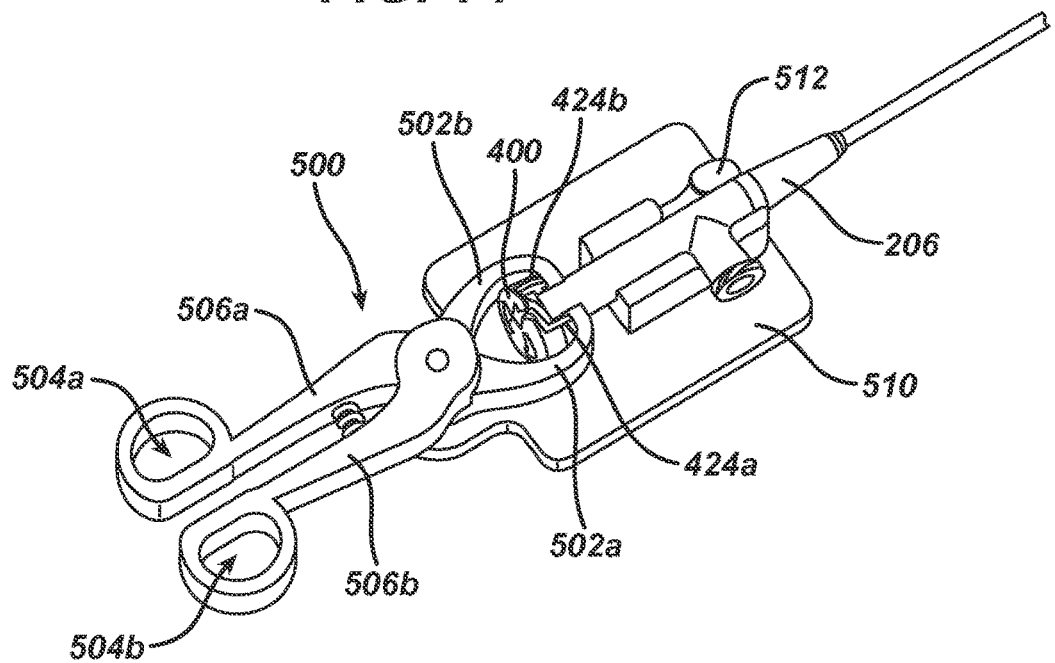
FIG. 14 is a simplified view of a representative vent cap removal device according to the invention.

Although the vent cap 400 and proximal connector 206 with differing types of connectors have been described for use in Eustachian tube dilation, these systems would be useful for other applications where balloon dilation of other ear, nose and throat anatomies is possible. Such anatomies include but are not limited the sinuses, including the maxillary sinus, frontal sinus, sphenoid sinus and ethmoid sinus, the related paranasal systems and sinus ostia and passageways, the middle ear, and the airways. The vent cap and proximal connectors described would prevent inadvertent attachment of a dilation device to other than the inflation port. Where a removable vent cap is provided, a removal device 500 could be provided. A representative removal device is shown in FIG. 14. The proximal connector 206 is shown mounted on a holding plate 510, the proximal connector being snapped into holding fixture 512. The removal device 500 is shown engaged with the proximal connector 206. In this embodiment, the engagement features are lever arms 502a and 502b which are engaged with the side arms 424a and 424b of the proximal connector 206 such that when the operator inserts the thumb and/or fingers into openings 504a and 504b and expands the removal device arms 506a and 506b apart at the removal device proximal end, the lever arms 502a and 502b exert force on the side arms 424a and 424b, forcing the side arms apart from the proximal connector 206 and causing disengagement of the side arms 422a and 422b from the in-line port 236 of the proximal connector 206 and removal of the vent cap 400 from the balloon catheter 200.

Figure 15:
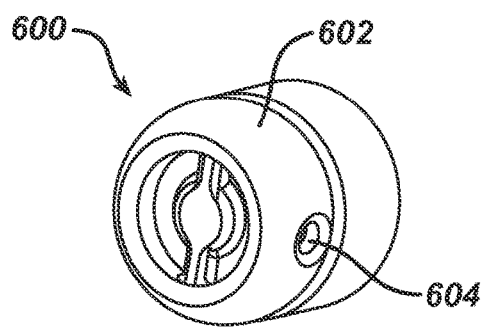
FIG. 15 is an isometric view of an alternative vent cap embodiment according to the invention.

FIG. 15 shows an alternative embodiment of a vent cap 600 according to the invention. Rather than the side arms shown in FIGS. 13A and 13B, the side portion 602 is a dome shaped member with a vent hole 604. The vent cap 600 may be attached to the balloon catheter in-line port 236 in a threaded arrangement, or by snap or friction fit. The vent cap 600 may be reversibly or irreversibly attached as noted above with regard to vent cap 400.

Figure 16A:
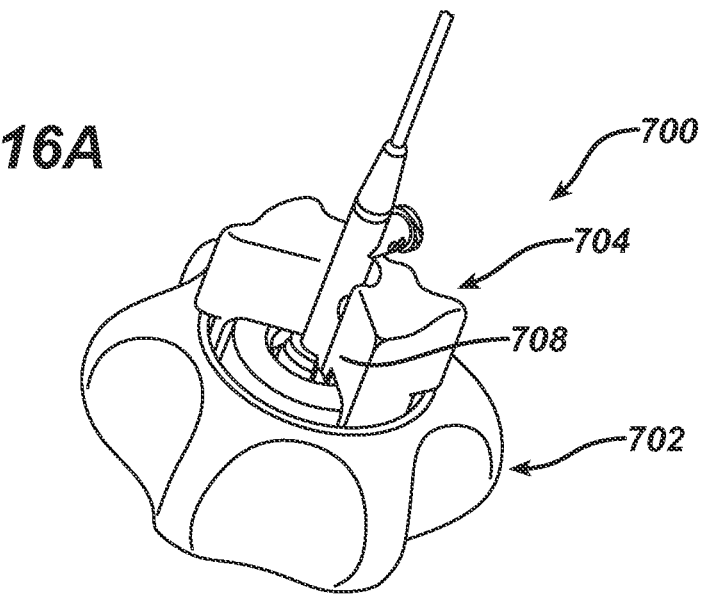
FIG. 16A is an isometric view of an alternative vent cap removal device according to the invention.
Figure 16B:
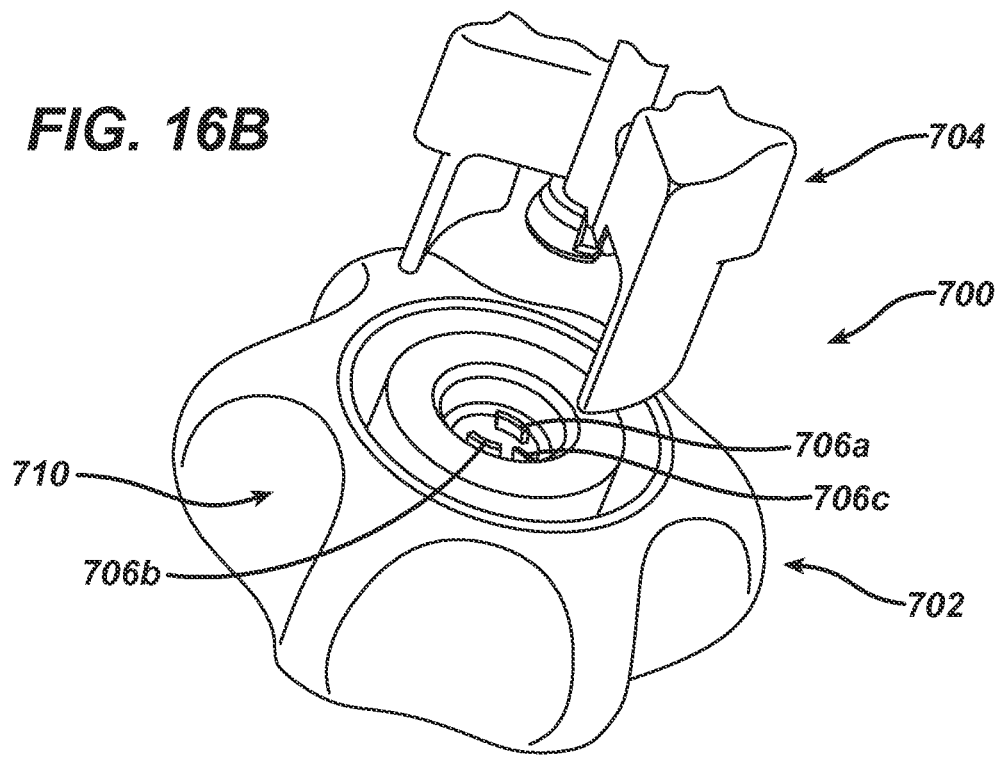
FIG. 16B is an exploded view of the vent cap removal device shown in FIG. 16A.

FIGS. 16A and 16B show an alternative embodiment of a vent cap removal device 700 according to a further embodiment of the invention. This removal device 700 includes a handle 702 and a holding fixture 704. Referring to vent cap 400 shown in FIG. 13B, the assembled balloon catheter 200 and vent cap 400 is inserted into the removal device 700 such that the top portion 420 of the vent cap 400 is seated in the handle 702 with the vent cap keys 706a, 706b and 706c aligned with the vent holes 406a, 406b, and 410. Once seated in the handle 702 and snapped into place in the holding fixture 704, the handle 702 is rotated, thereby engaging the engagement feature, in this case holding fixture edge 708 with the vent cap side arm 422a, forcing the vent cap arm 422a away from the proximal connector 206, such that the proximal connector 206 can be removed from the vent cap 400. The holding fixture edge 708 functions by using a cam action as a spreading mechanism of the vent cap arm 422a during rotation. Finger hold features 710 on the handle 702 allow for ease of holding the handle 702 and rotation of the handle 702 relative to the holding fixture 704.

As noted earlier, prior to or following balloon dilation, it may be desirable to inject solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), a surfactant, an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like.

Some nonlimiting examples of antimicrobial agents that may be used in this invention include acyclovir, amantadine, aminoglycosides (e.g., amikacin, gentamicin and tobramycin), amoxicillin, amoxicillinlclavulanate, amphotericin B, ampicillin, ampicillinlsulbactam, atovaquone, azithromycin, cefazolin, cefepime, cefotaxime, cefotetan, cefpodoxime, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscamet, ganciclovir, atifloxacin, imipenemlcilastatin, isoniazid, itraconazole, ketoconazole, metronidazole, nafcillin, nafcillin, nystatin, penicillin, penicillin G, pentamidine, piperacillinltazobactam, rifampin, quinupristindalfopristin, ticarcillinlclavulanate, trimethoprimlsulfamethoxazole, valacyclovir, vancomycin, mafenide, silver sulfadiazine, mupirocin (e.g., Bactroban, Glaxo SmithKline, Research Triangle Park, N.C.), nystatin, triamcinolonelnystatin, clotrimazolelbetamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfcgol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies"; agents which change the condition of the tissue to make it hostile to the pathogen (such as substances which alter mucosal pH (e.g., Buffer Gel and Acid form); non-pathogenic or "friendly" microbes that cause the production of hydrogen peroxide or other substances that kill or inhibit the growth of pathogenic microbes (e.g., lactobacillus): antimicrobial proteins or peptides such as those described in U.S. Pat. No. 6,716,813 (Lin et al.,) which is expressly incorporated herein by reference or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDS), analgesic agents or antipyretic agents. For example, corticosteroids that have previously been administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as mesulide).

Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor) and d) SYK Kinase inhibitors such as an agent designated as "R-112" manufactured by Rigel Pharmaceuticals, Inc, South San Francisco, Calif.

Additionally or alternatively, in some applications, such as those where it is desired to shrink mucosal tissue, cause decongestion, or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine. In one particular embodiment, the substance delivered by this invention comprises a combination of an anti-inflammatory agent (e.g. a steroid or an NSAID) and a mucolytic agent.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chroma) and nedocromil.

Additionally or alternatively, in some applications such as those where it is desired to prevent or inhibit the effect of histamine, the substances delivered in this invention may include various antihistamines such as azelastine (e.g., Astylin) diphenhydramine, loratidine, etc.

Additionally or alternatively, in some embodiments such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsinlLEDTA, hyaluronidase, and tosyllysylchloromethane (TLCM).

Additionally or alternatively, in some applications such as those wherein it is desired to treat a tumor or cancerous lesion, the substances delivered in this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other antitumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazolc, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat). CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, 1MC-IC11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmetteguerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

In one embodiment, a local anesthetic, such as Lidocaine is injected through the injection lumen 234 prior to dilation of the Eustachian Tube. The injection lumen 234 can be used for venting during dilation so that pressure in the middle ear does not increase or decrease.

While preferred embodiments of the present invention have been shown and described herein, it will be obvious to those skilled in the art that such embodiments are provided by way of example only. Numerous variations, changes and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A system for use in dilating a Eustachian tube of a patient, the system comprising:
    a balloon dilation catheter for accessing and treating the Eustachian tube through the nose of a human patient, the balloon dilation catheter comprising:
        (i) an elongate shaft, the elongate shaft having a proximal end and a distal end and an inflation lumen therebetween, the elongate shaft defining a longitudinal axis;
        (ii) an inflatable balloon positioned at the distal end of said elongate shaft;
        (iii) a proximal connector positioned at the proximal end of said elongate shaft, said proximal connector comprising an inflation port in fluid communication with the inflation lumen of the elongate shaft and an in-line port, the inflation port being oriented transversely relative to the longitudinal axis, the in-line port being coaxially aligned with the longitudinal axis; and
        (iv) a vent cap attached to said in-line port, the vent cap being coaxially aligned with the longitudinal axis, wherein the vent cap comprises a top portion and a central post, wherein the central post is dimensioned for insertion into the in-line port along the longitudinal axis, the central post defining a plurality of leaves extending outwardly from the longitudinal axis, and wherein vent cap further comprises a side portion with at least two side arms with gripping features for gripping to the in-line port, the vent cap further including at least one vent opening positioned laterally relative to the central post, the vent cap further defining a ventilation passageway between the at least one vent opening and open spaces defined between the leaves.

2. The system of claim 1 wherein the attachment of the vent cap to the in-line port is reversible.

3. The system of claim 1 wherein the vent is fixedly attached to the in-line port.

4. A dilation catheter comprising:
    (a) an elongate shaft defining a longitudinal axis, the elongate shaft including:
        (i) a proximal end,
        (ii) a distal end,
        (iii) an inflation lumen, and
        (iv) a second lumen separate from the inflation lumen;
    (b) an inflatable balloon positioned at the distal end of the elongate shaft, the inflatable balloon being in fluid communication with the inflation lumen;
    (c) a connector positioned at the proximal end of the elongate shaft, the connector including:
        (i) a first port positioned along the longitudinal axis of the elongate shaft, the first port being in fluid communication with the second lumen, and
        (ii) a second port oriented transversely relative to the longitudinal axis of the elongate shaft, the second port being in fluid communication with the inflation lumen;
    (d) a vent cap secured to the first port, the vent cap including:
        (i) a central post disposed in the first port, the central post being positioned along the longitudinal axis of the elongate shaft, the central post defining a plurality of leaves extending outwardly from the longitudinal axis, and
        (ii) at least one vent opening, the at least one vent opening being offset from the longitudinal axis of the elongate shaft, the at least one vent opening being in fluid communication with the second lumen, the vent cap further defining a ventilation passageway between the at least one vent opening and open spaces defined between the leaves.

5. The dilation catheter of claim 4, the plurality of leaves comprising three leaves extending outwardly from the longitudinal axis.

6. The dilation catheter of claim 5, the three leaves being sized and configured to fit inside the first port.

7. The dilation catheter of claim 4, wherein the at least one vent opening includes a notch extending radially inwardly from an outer perimeter of the vent cap.

8. The dilation catheter of claim 4, the vent cap further comprising at least one latch arm configured to latch onto the connector.

9. The dilation catheter of claim 4, the vent cap further comprising at least one stand-off feature, the at least one stand-off feature being configured to prevent the vent cap from sealing against first port.

10. The dilation catheter of claim 4, the vent cap further comprising a guidewire lumen.

* * * * *